(12) United States Patent
Antonucci

(10) Patent No.: US 8,217,081 B2
(45) Date of Patent: Jul. 10, 2012

(54) POLYMERIZABLE BIOMEDICAL COMPOSITION

(75) Inventor: Joseph M. Antonucci, Kensington, MD (US)

(73) Assignee: The United States of America as represented by the Secretary of Commerce, The National Institute of Standards and Technology, Washington, DC (US)

( * ) Notice: Subject to any disclaimer, the term of this patent is extended or adjusted under 35 U.S.C. 154(b) by 304 days.

(21) Appl. No.: 12/647,661

(22) Filed: Dec. 28, 2009

(65) Prior Publication Data

US 2010/0256242 A1 Oct. 7, 2010

Related U.S. Application Data

(60) Provisional application No. 61/167,180, filed on Apr. 7, 2009.

(51) Int. Cl.
*A01N 33/12* (2006.01)
*C07C 69/52* (2006.01)
(52) U.S. Cl. ........................................ 514/642; 560/222
(58) Field of Classification Search .................. 514/642; 560/220, 222
See application file for complete search history.

(56) References Cited

U.S. PATENT DOCUMENTS

| | | | |
|---|---|---|---|
| 3,926,870 A | 12/1975 | Keegan et al. | |
| 4,013,507 A | 3/1977 | Rembaum | |
| 4,873,269 A | 10/1989 | Nakazato | |
| 4,970,211 A | 11/1990 | Fenyes et al. | |
| 5,102,874 A | 4/1992 | Lintner et al. | |
| 5,866,631 A | 2/1999 | Nakagawa et al. | |
| 6,077,698 A | 6/2000 | Swan et al. | |
| 6,403,671 B1 | 6/2002 | May et al. | |
| 6,482,969 B1 | 11/2002 | Helmrick et al. | |
| 2008/0039592 A1 | 2/2008 | Sawada et al. | |

OTHER PUBLICATIONS

Xiao, et al., Antibacterial Effects of Three Experimental Quaternary Ammonium Salt (QAS) Monomers on Bacteria Associated With Oral Infections, Journal of Oral Science, vol. 50, No. 3, 323-327, 2008, pp. 323-327.
Li, et al., Effects of a Dental Adhesive Incorporating Antibacterial Monomer on the Growth, Adherence and Membrane Integrity of *Streptococcus mutans*, Journal of Dentistry 37 (2009), pp. 289-296.
Beyth, et al., Antibacterial Activity of Dental Composites Containing Quaternary Ammonium Polyethylenimine Nanoparticles Against *Streptococcus mutans*, Biomaterials 27 (2006), pp. 3995-4002.

*Primary Examiner* — Raymond Henley, III
(74) *Attorney, Agent, or Firm* — Carlson, Gaskey & Olds, P.C.

(57) ABSTRACT

A polymerizable biomedical composition includes a quaternary ammonium group bonded at its quaternary sites to respective groups $R_1$, $R_2$, $R_3$, and $R_4$. $R_1$ and $R_2$ each include a vinyl moiety such that the composition is at least bi-functional with respect to polymerization.

19 Claims, No Drawings

POLYMERIZABLE BIOMEDICAL COMPOSITION

CROSS-REFERENCE TO RELATED APPLICATIONS

This application claims priority to U.S. Provisional Application No. 61/167,180, filed on Apr. 7, 2009.

BACKGROUND

This disclosure relates to bio-affecting compositions for attenuating propagation of bacteria in such applications as dental materials.

In the area of biomedical materials, and specifically within dental composites, a variety of different anti-bacterial materials have been investigated. As an example, researchers have developed materials with anti-bacterial agents, such as silver ions. These types of materials have limited effectiveness because the anti-bacterial properties depend upon the release of the anti-bacterial agent from the material. The effectiveness therefore declines over time as the anti-bacterial agent depletes.

More recently, researchers have developed another class of biomedical material in the form of a polymerizable monomer that includes a quaternary ammonium salt. Although this composition has apparently demonstrated some effectiveness, the monomer is a solid at ambient conditions and has limited compatibility with biomedical resins.

SUMMARY OF THE INVENTION

An exemplary polymerizable biomedical composition includes a quaternary ammonium group bonded at its quaternary sites to respective groups $R_1$, $R_2$, $R_3$, and $R_4$. $R_1$ and $R_2$ each include a vinyl moiety such that the composition is at least bifunctional with respect to polymerization.

In another aspect, a polymerizable biomedical composition may include a biomedical resin that is mixed with a anti-bacterial composition such that, when initiated, the biomedical resin and the anti-bacterial composition polymerize to form a co-polymer. The anti-bacterial composition includes a quaternary ammonium group bonded to respective groups $R_1$, $R_2$, $R_3$, and $R_4$. $R_1$ and $R_2$ each include a vinyl moiety such that the anti-bacterial composition is at least bi-functional with respect to polymerization of the mixture.

An exemplary method of producing a polymerizable biomedical composition includes reacting a tertiary amine with an organo-halide to produce a reaction product that includes a quaternary ammonium group bonded to respective groups $R_1$, $R_2$, $R_3$, and $R_4$. $R_1$ and $R_2$ each include a vinyl moiety such that the polymerizable biomedical composition is at least bifunctional with respect to polymerization.

DETAILED DESCRIPTION OF THE PREFERRED EMBODIMENT

Disclosed are exemplary polymerizable biomedical compositions (hereafter "compositions") that include a quaternary ammonium group that is bonded at its quaternary sites to respective groups $R_1$, $R_2$, $R_3$, and $R_4$. In this case, the nomenclature $R_{1-4}$ refers to the bonding position of the respective group on the nitrogen atom. As will be appreciated, the bonding angles and spatial orientation may vary depending on the chemistry of the groups $R_{1-4}$. As an example, this disclosure assumes the following configuration, which may vary in other examples:

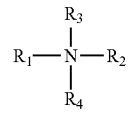

As will be described in further detail, $R_1$ and $R_2$ each include a vinyl group such that the composition is at least bifunctional with respect to polymerization. In comparison, one drawback of a monofunctional composition is that the composition forms a linear polymeric structure that is susceptible to leaching from the final compositions are also typically in solid form at ambient temperatures and pressures and therefore are not readily compatible with known biomedical resins. However, with the chemical structure and bifunctionality of the disclosed compositions, the vinyl groups on each of the $R_1$ and $R_2$ groups function as polymerization sites and result in a cross-linking of the material with biomedical resins such that the composition is less susceptible to leaching and maintains the anti-bacterial properties.

As an example, the exemplary polymerizable biomedical compositions may be used as a resin, monomer, or oligomer for polymerization with a biomedical resin. The type of biomedical resin is not limited to any particular field but use in the area of dental materials is contemplated to form a dental adhesive or composite. For instance, the composition may be used with dental resins of various types, such as acrylic-based resins with hydrocarbon, ether, fluorocarbon, siloxane, urethane, or other types of segments known and used in polymeric dental materials such as composites, adhesives and sealants.

Dental resins typically exhibit a volumetric shrinkage upon polymerization that may result in a gap between the material and the tooth. The gap may be infiltrated by bacteria that propagate to eventually develop secondary or recurrent caries or tooth decay at the tooth-material interface. However, with the disclosed compositions having anti-bacterial properties, the propagation of any bacteria may be reduced, limited, or eliminated to thereby facilitate reducing caries or tooth decay.

In one example, a polymerizable biomedical composition may be produced through adaption of a Menschutkin reaction to react a tertiary amine with an organo-halide. A generic form of the reaction is shown below in equation (1).

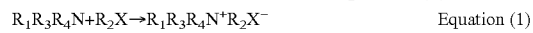

where halogen X=F, Cl, Br, or I

Thus, by selecting $R_1$ and $R_2$ to include vinyl groups, the composition can be produced with bifunctionality relative to polymerization.

The chemical structure of the composition may be selected to be compatible with known types of dental resins or other biomedical resins. As an example, the composition may be selected to be compatible with acrylic or acrylic urethane resins by including acrylic or acrylic urethane groups that are bonded to the quaternary ammonium group. The compatibility thereby increases the miscibility of the compositions in biomedical resins of interest. The following examples illustrate several reaction schemes for producing an acrylic type of composition. However, it is to be understood that the reactions can also be adapted for other types of groups in dental or biomedical resins.

Reaction A illustrated below illustrates the quaternization of an amino methacryl starting material to produce a non-fluorinated type of the anti-bacterial composition, indicated as IDMA-1. To produce IDMA-1, in a tared vial equipped with a magnetic stir bar was placed 1.57 g (10 mmol) of 2-(N,N-dimethylamino)ethyl methacrylate (DMAEMA), 1.93 g (10 mmol) of 2-bromoethyl methacrylate (BEMA), and 3 g ethanol. The vial was capped, and the mixture was heated at 60° C. and stirred for 24 h. After removal of the solvent and residual reagents, a clear, colorless, viscous product (IDMA-1) was isolated in near quantitative yield. IDMA-1 includes acrylate groups as $R_1$ and $R_2$ (to the left and right, respectively, of the N atom in the illustration), and alkyl groups (e.g., methyl groups) as $R_3$ and $R_4$ (to the top and bottom, respectively, of the N atom in the illustration). In modified examples the IDMA-1 may include other alkyl groups for $R_3$ and $R_4$, such as ethyl groups or groups having more than two carbon atoms.

Reaction B illustrated below illustrates the quaternization of an amino methacryl starting material to produce another non-fluorinated type of the anti-bacterial composition, indicated as IDMA-3. IDMA-3 was synthesized in a similar manner as IDMA-1 from DMAEMA but using 2,2'-bis(bromomethyl)-1,1'-biphenyl (BbmBP) instead of the BEMA. IDMA-3 includes an acrylate group as $R_1$, a bis(benzyl) group as $R_2$, and alkyl groups (e.g., methyl groups) as $R_3$ and $R_4$.

nium includes groups $R_5$, $R_6$, $R_7$ and $R_8$ bonded at its quaternary sites. In this case, $R_7$ and $R_8$ (top and bottom, respectively) are the methyl groups, $R_5$ is an acrylate group, and $R_6$ is a bis(-1,1-biphenyl group (top and bottom, respectively).

Reaction C illustrated below illustrates the quaternization of an amino methacryl starting material to produce a polyfluorinated type of anti-bacterial composition. The polyfluorinated anti-bacterial composition was synthesized in a similar manner as IDMA-1 from DMAEMA but using polyfluoroalkanes with terminal halomethyl groups such as 2,2 3,3 4,4 5,5-octafluoro-1,6-diiodo-hexane instead of the BEMA or BbmBP. These polyfluorinated compounds are expected to be compatible with fluorinated acrylic monomers such as 2,2,3, 3,4,4,5,5,-octafluoro-1,6,-hexanedimethacrylate. This fluorinated anti-bacterial composition includes an acrylate group as $R_1$, a fluorine-containing group as $R_2$ (e.g., a fluorocarbon), and alkyl groups (e.g., methyl groups) as $R_3$ and $R_4$. Further, as can be seen in Reaction C, the group $R_2$ also includes a second quaternary ammonium bonded to the fluorine-containing group.

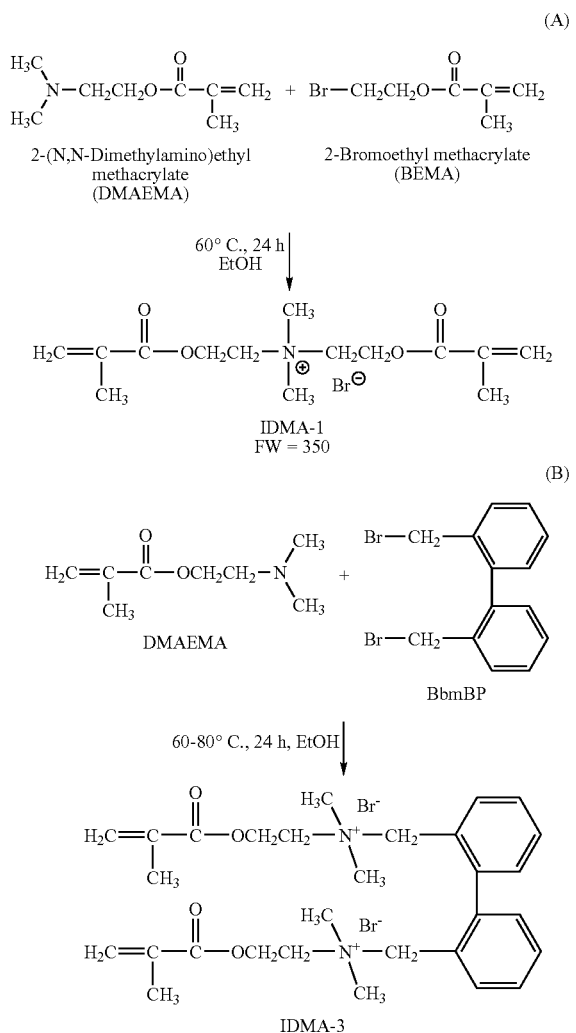

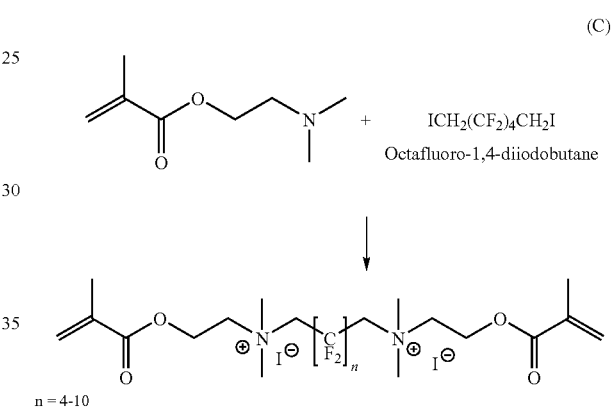

Further, as can be seen in Reaction B, the two halide sites of the BbmBP react such that $R_2$ also includes a second quaternary ammonium and another benzyl group (i.e., as a bis(methyl-1,1-biphenyl). This second quaternary ammo- The compositions as described above or other compositions produced by the disclosed method, may then be mixed with a biomedical resin of choice for eventual polymerization to form a biomedical polymer. In a few examples, the biomedical resin may be an acrylic resin, an acrylic urethane resin, or other type of acrylic resin that is suitable for use in contact with the human body. In some examples, the biomedical resin may be chosen from triethylene glycol dimethacrylate (TEGDMA), 2/2-bis[p-(2'-hydroxy3' methacryloxypropoxy)phenyl]propane (bis-GMA), or mixtures thereof. Fillers, such as reinforcing agents (e.g., glass, mineral, etc.), may also be added to the mixture in a desired amount. In other examples, a fluorinated type of the anti-bacterial composition may be mixed with a fluorinated biomedical resin. The fluorinated group in the anti-bacterial composition renders the composition compatible with the fluorinated biomedical resin to facilitate mixing without phase separation.

In a further example, the biomedical resin may include about 10-90 wt. % of the TEGDMA and about 10-90 wt. % of the bis-GMA, which may then be mixed with the polymerizable composition to form a mixture composition. That is, the mixture includes an amount $X_{TEGDMA}$ wt. % of the TEGDMA and an amount $X_{bis\text{-}GMA}$ wt. % of the bis-GMA, where $X_{TEGDMA}$ and $X_{bis\text{-}GMA}$ are each 10-90 wt. % and $X_{TEGDMA}$+$X_{bis\text{-}GMA}$ equals 100. In a further example, the biomedical resin may include about 40-60 wt. % of the TEGDMA and about 40-60 wt. % of the bis-GMA. The mixed composition may further include additives, fillers, and a polymerization initiator, such as a photo-initiator, to initiate polymerization upon exposure to a light source. As an example, the initiator may be camphorquinone and ethyl 4-N,N-dimethylaminobenzoate. However, it is to be understood that other types of initiators may be used depending upon the selected composition and the intended applications.

The disclosed compositions provide the advantage of being a liquid at room temperature and ambient pressure conditions, such as 23° C. and normal atmospheric pressure. That is, the target biomedical resins that are to be mixed with the composition are normally liquid or semi-liquid at such conditions and thereby readily mix with the composition such that the composition is miscible within the biomedical resin. As an example, the mixture of the biomedical resin and the composition may include up to about 50 wt. % of the composition. In comparison, a solid composition would be less miscible within a given biomedical resin. However, due to the liquid state of the disclosed compositions, more of the anti-bacterial composition may be included with the biomedical resins, resulting in a final material having a greater amount of quaternary ammonium sites.

In other examples, the mixture may include up to about 30 wt. % of the anti-bacterial composition, and more specifically, about 10% or 8-12% of the anti-bacterial composition. On a lower end, the mixture may include as little as about 1 wt.% of the anti-bacterial composition. Simply, the amount of anti-bacterial composition may depend upon the desired degree of anti-bacterial properties in the final polymer. In many cases, about 10% may be effective for limiting or ceasing propagation of bacterial activity. In this regard, the anti-bacterial compositions may be considered to be a modified ionene liquid or ionic liquid monomer. One premise of this disclosure is that the disclosed anti-bacterial compositions have a chemical structure that is bifunctional with regard to polymerization, are anti-bacterial, and are highly miscible because of their liquidity, thereby, promoting compatibility with typical biomedical resins. The liquid state may be attributed, at least in part, to the chemical structure of the disclosed anti-bacterial compositions. For instance, the $R_1$ and $R_2$ groups bonded to the ammonium site are sterically bulky and inhibit packing of the molecules to form solid structures. Additionally, the ammonium functionality may be susceptible to picking up water and, in the hydrated state, may be stable as a liquid material. However, the disclosed compositions may generally be more hydrophobic than hydrophilic, and are designed to be non-crystalline and based on the premise that "like dissolves like" so that miscibility is facilitated with typical dental resins.

Although a combination of features is shown in the illustrated examples, not all of them need to be combined to realize the benefits of various embodiments of this disclosure. In other words, a system designed according to an embodiment of this disclosure will not necessarily include all of the features shown in any one of the FIGURES or all of the portions schematically shown in the FIGURES. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A polymerizable biomedical composition comprising a quaternary ammonium group bonded at its quaternary sites to respective groups $R_1$, $R_2$, $R_3$, and $R_4$, where $R_1$ and $R_2$ each include a vinyl moiety such that the composition is at least bifunctional with respect to polymerization and where $R_3$ and $R_4$ are alkyl groups.

2. The composition as recited in claim 1, wherein $R_1$ and $R_2$ are acrylate groups.

3. The composition as recited in claim 2, wherein $R_1$ and $R_2$ are each methacrylates.

4. The composition as recited in claim 1, wherein at least one of $R_1$ or $R_2$ includes at least one of a benzyl group or a bis(methylphenyl group).

5. The composition as recited in claim 1, wherein $R_1$ includes an acrylate group and $R_2$ includes a second quaternary ammonium group bonded at its quaternary sites to respective groups $R_5$, $R_6$, $R_7$, and $R_8$, where $R_5$ is in an acrylate group having a vinyl moiety, $R_6$ includes a methyl phenyl groups, and $R_3$, $R_4$, $R_7$, and $R_8$ are alkyl groups.

6. The composition as recited in claim 1, wherein the composition is a liquid at 23° C. and ambient atmospheric pressure.

7. The composition as recited in claim 1, wherein $R_1$ is an acrylate group, $R_3$ and $R_4$ are alkyl groups, and $R_2$ is selected from a group consisting of acrylate and phenyl groups.

8. The composition as recited in claim 1, wherein the composition is non-fluorinated.

9. The composition as recited in claim 1, wherein $R_1$ is an acrylate group and $R_2$ is a fluorine-containing group.

10. A polymerizable biomedical composition comprising a biomedical resin mixed with an anti-bacterial composition such that, when initiated, the biomedical resin and the anti-bacterial composition polymerize to form a copolymer, the anti-bacterial composition including a quaternary ammonium group bonded to respective groups $R_1$, $R_2$, $R_3$, and $R_4$, and $R_1$ and $R_2$ each include a vinyl moiety such that the anti-bacterial composition is at least bifunctional with respect to polymerization of the mixture and where $R_3$ and $R_4$ are alkyl groups.

11. The composition as recited in claim 10, wherein the mixture of the biomedical resin and the anti-bacterial composition further includes an initiator operative to initiate polymerization between the biomedical resin and the anti-bacterial composition.

12. The composition as recited in claim 10, wherein the mixture includes up to about 30 wt.% of the anti-bacterial composition, and the anti-bacterial composition is non-fluorinated.

13. The composition as recited in claim 12, wherein the mixture includes up to about 15 wt.% of the anti-bacterial composition.

14. The composition as recited in claim 13, wherein the mixture includes 10 wt.% of the anti-bacterial composition.

15. The composition as recited in claim 13, wherein the mixture includes 8-12 wt.% of the anti-bacterial composition.

16. The composition as recited in claim 10, wherein the biomedical resin is selected from a group consisting of triethylene glycol dimethacrylate (TEGDMA), 2/2-bis[p-(2'-hydroxyl-3'methacryloxypropoxy) phenyl] propane (bis-GMA), and mixtures thereof.

17. The composition as recited in claim 16, wherein the mixture includes an amount $X_{TEGDMA}$ wt.% of the TEGDMA and an amount $X_{bis\text{-}GMA}$ wt.% of the bis-GMA, where $X_{TEGDMA}$ and $X_{bis\text{-}GMA}$ are each 10-90wt.% and $X_{TEGDMA} + X_{bis\text{-}GMA}$ equals 100.

18. The composition as recited in claim 10, wherein the mixture is a liquid at a temperature of 23° C. and ambient atmospheric pressure.

19. A method of producing a polymerizable biomedical composition, comprising:
   reacting a tertiary amine with an organo-halide to produce a reaction product that includes a quaternary ammonium group bonded to respective groups $R_1$, $R_2$, $R_3$, and $R_4$, where $R_1$ and $R_2$ each include a vinyl moiety such that the polymerizable biomedical composition is at least bifunctional with respect to polymerization and where $R_3$ and $R_4$ are alkyl groups.

* * * * *